United States Patent
Aiki et al.

(10) Patent No.: US 10,427,139 B2
(45) Date of Patent: Oct. 1, 2019

(54) METHOD FOR PRODUCING AMMOXIDATION CATALYST, AND METHOD FOR PRODUCING ACRYLONITRILE

(71) Applicant: ASAHI KASEI KABUSHIKI KAISHA, Tokyo (JP)

(72) Inventors: Shota Aiki, Tokyo (JP); Akiyoshi Fukuzawa, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/772,562

(22) PCT Filed: Apr. 26, 2017

(86) PCT No.: PCT/JP2017/016631
§ 371 (c)(1),
(2) Date: May 1, 2018

(87) PCT Pub. No.: WO2017/188349
PCT Pub. Date: Nov. 2, 2017

(65) Prior Publication Data
US 2019/0091666 A1    Mar. 28, 2019

(30) Foreign Application Priority Data

Apr. 27, 2016  (JP) ................ 2016-089582

(51) Int. Cl.
| | | |
|---|---|---|
| *B01J 23/887* | (2006.01) | |
| *B01J 37/04* | (2006.01) | |
| *B01J 37/08* | (2006.01) | |
| *C07C 253/26* | (2006.01) | |
| *C07C 255/08* | (2006.01) | |
| *B01J 37/03* | (2006.01) | |
| *B01J 37/06* | (2006.01) | |
| *B01J 23/00* | (2006.01) | |
| *B01J 37/00* | (2006.01) | |

(52) U.S. Cl.
CPC ......... *B01J 23/8876* (2013.01); *B01J 23/002* (2013.01); *B01J 23/887* (2013.01); *B01J 37/0045* (2013.01); *B01J 37/035* (2013.01); *B01J 37/04* (2013.01); *B01J 37/06* (2013.01); *B01J 37/08* (2013.01); *C07C 253/26* (2013.01); *C07C 255/08* (2013.01); *B01J 2523/00* (2013.01); *Y02P 20/52* (2015.11)

(58) Field of Classification Search
None
See application file for complete search history.

(56) References Cited

U.S. PATENT DOCUMENTS

| | | |
|---|---|---|
| 4,166,808 A | 9/1979 | Daumas et al. |
| 4,978,765 A | 12/1990 | Sasaki et al. |
| 2006/0155139 A1 | 7/2006 | Yanagi et al. |
| 2013/0023699 A1 | 1/2013 | Macht et al. |
| 2015/0238939 A1 | 8/2015 | Yoshida et al. |

FOREIGN PATENT DOCUMENTS

| | | |
|---|---|---|
| DE | 10 2011 079 0305 A1 | 1/2013 |
| JP | 01-265068 A | 10/1989 |
| JP | 2000-042414 A | 2/2000 |
| JP | 2006-055732 A | 3/2006 |
| JP | 2008-212779 A | 9/2008 |
| JP | 2013-017917 A | 1/2013 |
| JP | 2013-169482 A | 9/2013 |
| TW | 200427509 A | 12/2004 |
| WO | WO 2013/007736 A1 | 1/2013 |
| WO | WO 2014/051090 A1 | 4/2014 |

OTHER PUBLICATIONS

Supplementary European Search Report dated Apr. 17, 2019, in European Patent Application No. 17789631.3.
International Search Report for PCT/JP2017/016631 (PCT/ISA/210) dated Aug. 1, 2017.
Written Opinion of the International Searching Authority for PCT/JP2017/016631 (PCT/ISA/237) dated Aug. 1, 2017.
English translation of International Preliminary Report on Patentability and Written Opinion dated Nov. 8, 2018, in PCT/JP2017/016631 (Forms PCT/IB/326, PCT/IB/373, and PCT/ISA/237).

*Primary Examiner* — Kamal A Saeed
(74) *Attorney, Agent, or Firm* — Birch, Stewart, Kolasch & Birch, LLP

(57) ABSTRACT

A method for producing an ammoxidation catalyst, comprising:
a step of preparing a precursor slurry that is a precursor of the catalyst;
a drying step of obtaining a dry particle from the precursor slurry; and
a calcination step of calcining the dry particle, wherein
the step of preparing the precursor slurry is a step of mixing a first solution or slurry having a first pH and a second solution or slurry to obtain a solution or slurry having a second pH after completion of mixing,
a time during which a pH of a mixture passes through a particular range having an upper limit and a lower limit while the second solution or slurry is mixed is 1-70 seconds, the upper limit and the lower limit being designated as a third pH and a fourth pH respectively, and
the third pH and the fourth pH are set between the first pH and the second pH.

7 Claims, 2 Drawing Sheets

[Figure 1]
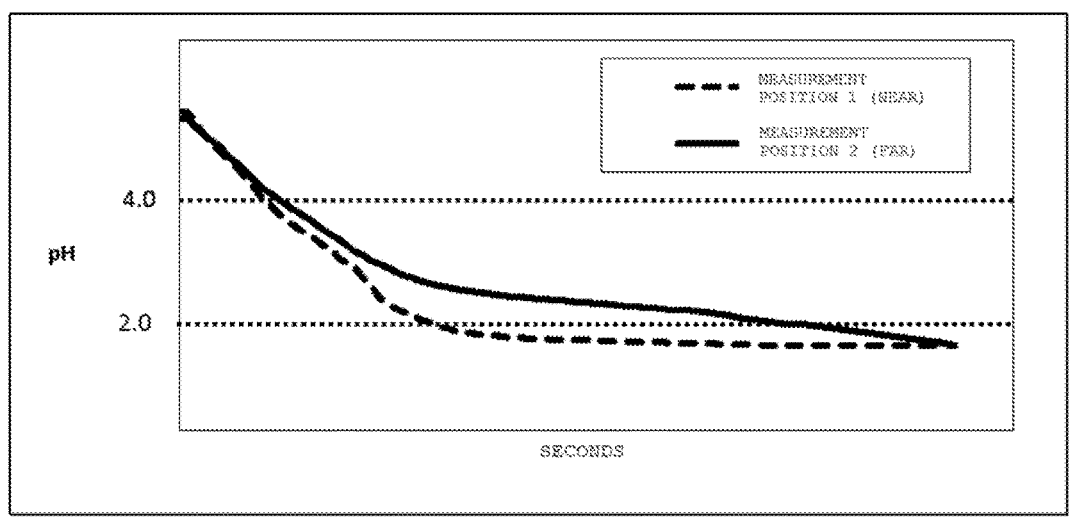

[Figure 2]
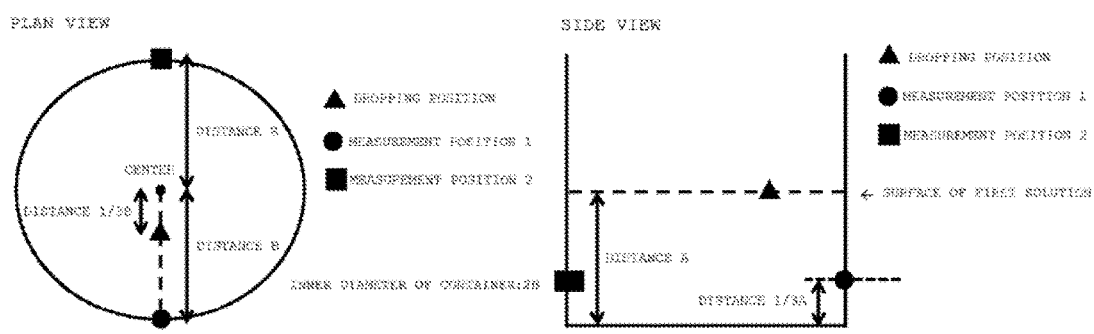

METHOD FOR PRODUCING AMMOXIDATION CATALYST, AND METHOD FOR PRODUCING ACRYLONITRILE

TECHNICAL FIELD

The present invention relates to a method for producing an ammoxidation catalyst, and a method for producing acrylonitrile.

BACKGROUND ART

A reaction in which propylene and ammonia are reacted in the presence of molecular oxygen to produce acrylonitrile is known as an "ammoxidation reaction", and this reaction is used as an industrial production method for acrylonitrile.

In this reaction, a catalyst is utilized in order to achieve a good acrylonitrile yield. For example, many catalysts comprising Mo—Bi—Fe or Fe—Sb as essential components are industrially used. Catalysts to which not only such essential components but other elements are added in order to achieve a better acrylonitrile yield are known (for example, see Patent Documents 1 and 2).

On the other hand, attempts are also made to improve the yield of acrylonitrile by making improvements in the step of preparing a catalyst though the element components constituting the catalyst are common. Patent Document 3 discloses a method involving adjusting a slurry at pH 5 or less and heat-treating the slurry at 50-120° C., and Patent Document 4 discloses a method involving adjusting a slurry at pH 6 or more and heat-treating the slurry at 50-120° C., and the like.

LIST OF PRIOR ART DOCUMENTS

Patent Document

Patent Document 1: Japanese Patent Laid-Open No. 2013-169482
Patent Document 2: Japanese Patent Laid-Open No. 2008-212779
Patent Document 3: Japanese Patent Laid-Open No. 1-265068
Patent Document 4: Japanese Patent Laid-Open No. 2000-42414

SUMMARY OF INVENTION

Problems to be Solved by Invention

In the development of ammoxidation catalysts, changes in the metal composition have been repeated up to the present, and in recent years, it has been difficult to achieve a great improvement in yield with only improvements in the composition. In contrast to this, the acrylonitrile yield improves gradually by improvements in the step of preparing a catalyst, but a satisfactory yield is not necessarily obtained yet.

The present invention has been made in view of the above problems, and it is an object of the present invention to provide a method for producing an ammoxidation catalyst that exhibits a high acrylonitrile yield, and a method for producing acrylonitrile.

Means for Solving Problems

The present inventors have studied in order to solve the above problems, and as a result found that the problems can be solved by a method for producing a catalyst comprising the step of mixing a first solution or slurry having a first pH and a second solution or slurry to prepare a precursor slurry that is a precursor of the catalyst, the time during which a pH of the mixture passes through a particular pH range is adjusted in a particular range, thereby completing the present invention.

Specifically, the present invention is as follows.

[1]
A method for producing an ammoxidation catalyst, comprising:
a step of preparing a precursor slurry that is a precursor of the catalyst;
a drying step of obtaining a dry particle from the precursor slurry; and
a calcination step of calcining the dry particle, wherein
the step of preparing the precursor slurry is a step of mixing a first solution or slurry having a first pH and a second solution or slurry to obtain a solution or slurry having a second pH after completion of mixing,
a time during which a pH of a mixture passes through a particular range having an upper limit and a lower limit while the second solution or slurry is mixed is 1-70 seconds, the upper limit and the lower limit being designated as a third pH and a fourth pH respectively, and
the third pH and the fourth pH are set between the first pH and the second pH.

[2]
The method for producing the ammoxidation catalyst according to the above [1], wherein
the step of preparing the precursor slurry is a step of mixing a second solution or slurry comprising at least bismuth and iron with a first solution or slurry comprising at least molybdenum to obtain a precursor slurry,
a pH of the first solution or slurry before the second solution or slurry is mixed is within a range of 5.5-7.0,
a pH of the first solution or slurry after mixing of the second solution or slurry is completed is within a range of 0.1-1.9, and
a time during which a pH of a mixture passes through a range of 4.0-2.0 while the second solution or slurry is mixed is 1-70 seconds.

[3]
The method for producing the ammoxidation catalyst according to the above [1], wherein
the step of preparing the precursor slurry is a step of mixing a second solution or slurry comprising at least molybdenum with a first solution or slurry comprising at least bismuth and iron to obtain a precursor slurry,
a pH of the first solution or slurry before the second solution or slurry is mixed is within a range of 0.1-0.5,
a pH of the first solution or slurry after mixing of the second solution or slurry is completed is within a range of 0.7-1.9, and
a time during which a pH of a mixture passes through a range of 0.5-0.7 while the second solution or slurry is mixed is 1-70 seconds.

[4]
The method for producing the ammoxidation catalyst according to any of the above [1]-[3], wherein
a volume of the precursor slurry is 10 L or more, a time during which the pH of the mixture passes through the particular range at an outermost peripheral position in a container nearest to a position where the second solution or slurry is added while the second solution or slurry is mixed is designated as a first time, a time during which the pH of the mixture passes through the particular range at an outermost peripheral position in the container farthest from the position where the second solution or slurry is added while the second solution or slurry is mixed is designated as a second time, the first time is within a range of 1-70 seconds, and
a ratio of the second time to the first time is 3 or less.

[5]
The method for producing the ammoxidation catalyst according to any of the above [2]-[4], wherein in the step of preparing the precursor slurry, the solution or slurry comprising at least molybdenum comprises at least silica.

[6]
The method for producing the ammoxidation catalyst according to any of the above [1]-[5], wherein the ammoxidation catalyst comprises a metal oxide having a composition represented by the following general formula (1), and a support containing silica,

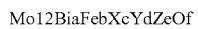  (1)

wherein X represents one or more elements selected from nickel, cobalt, magnesium, calcium, zinc, strontium, and barium, Y represents one or more elements selected from cerium, chromium, lanthanum, neodymium, yttrium, praseodymium, samarium, aluminum, gallium, and indium, Z represents one or more elements selected from potassium, rubidium, and cesium, $0.1 \leq a \leq 2.0$, $0.1 \leq b \leq 3.0$, $0.1 \leq c \leq 10.0$, $0.1 \leq d \leq 3.0$, $0.01 \leq e \leq 2.0$, and f is a number of atoms of oxygen necessary to satisfy valence requirements of other elements present.

[7]
A method for producing acrylonitrile, comprising reacting propylene, molecular oxygen, and ammonia, wherein the ammoxidation catalyst produced by the method according to any of the above [1]-[6] is used.

Advantages of Invention

According to the present invention, a method for producing an ammoxidation catalyst that exhibits a high acrylonitrile yield and high propylene activity in the ammoxidation reaction of propylene, and a high yield method for producing acrylonitrile can be provided.

BRIEF DESCRIPTION OF DRAWINGS

FIG. 1 is a conceptual diagram showing differences in changes in pH between measurement positions.
FIG. 2 is a diagram schematically showing a second solution dropping position and pH measurement positions in a container in Example 1 and Example 21.

MODE FOR CARRYING OUT INVENTION

A mode for carrying out the present invention (hereinafter simply referred to as the "present embodiment") will be described below. However, the present invention is not limited to the following embodiment, and various modifications can be made without departing from the spirit thereof.

[Method for Producing Ammoxidation Catalyst]
A method for producing an ammoxidation catalyst in the present embodiment is
a method for producing an ammoxidation catalyst, comprising:
the step of preparing a precursor slurry that is a precursor of a catalyst;

the drying step of obtaining dry particles from the precursor slurry; and
the calcination step of calcining the dry particles, wherein
the step of preparing a precursor slurry is the step of mixing a first solution or slurry having a first pH and a second solution or slurry to obtain a solution or slurry having a second pH after the completion of the mixing,
the time during which the pH of the mixture passes through a particular range having an upper limit and a lower limit while the second solution or slurry is mixed is 1-70 seconds, the upper limit and the lower limit being designated as a third pH and a fourth pH, and
the third pH and the fourth pH are set between the first pH and the second pH.

Here, the phrase "set between" also includes a case where the values of the third pH or the fourth pH are the same as the value of the first pH or the second pH.

In a preferred mode of the method for producing an ammoxidation catalyst in the present embodiment, the step of preparing a precursor slurry is the step of mixing a second solution or slurry comprising at least bismuth and iron with a first solution or slurry comprising at least molybdenum to obtain a precursor slurry, the pH of the first solution or slurry before the second solution or slurry is mixed is within the range of 5.5-7.0, the pH of the first solution or slurry after the mixing of the second solution or slurry is completed is within the range of 0.1-1.9, and the time during which the pH of the mixture passes through the range of 4.0-2.0 while the second solution or slurry is mixed is 1-70 seconds. This production method is referred to as the "first preparation method".

Examples of the metal contained in the first solution or slurry having a first pH in the first preparation method include molybdenum.

The first pH is preferably 5.5-6.7, more preferably 5.6-6.5, and further preferably 5.7-6.3.

Examples of the metal contained in the second solution or slurry in the first preparation method include bismuth, iron, and nickel.

The second pH in the first preparation method is preferably 0.2-1.8, more preferably 0.3-1.6, and further preferably 0.4-1.4.

In another preferred mode of the method for producing an ammoxidation catalyst in the present embodiment, the step of preparing a precursor slurry is the step of mixing a second solution or slurry comprising at least molybdenum with a first solution or slurry comprising at least bismuth and iron to obtain a precursor slurry, the pH of the first solution or slurry before the second solution or slurry is mixed is within the range of 0.1-0.5, the pH of the first solution or slurry after the mixing of the second solution or slurry is completed is within the range of 0.7-1.9, and the time during which the pH of the mixture passes through the range of 0.5-0.7 while the second solution or slurry is mixed is 1-70 seconds. This production method is referred to as the "second preparation method".

Examples of the metal contained in the first solution or slurry having a first pH in the second preparation method include bismuth, iron, and nickel.

The first pH is preferably 0.15-0.45, more preferably 0.20-0.40, and further preferably 0.25-0.35.

Examples of the metal contained in the second solution or slurry in the second preparation method include molybdenum.

The second pH in the second preparation method is preferably 0.8-1.8, more preferably 0.9-1.6, and further preferably 1.0-1.4.

In the production method in the present embodiment, the time during which the pH of the mixture passes through the particular range having an upper limit and an lower limit while the second solution or slurry is mixed is adjusted at 1-70 seconds, the upper limit and the lower limit being designated as a third pH and a fourth pH respectively. Here, "the pH of the mixture" refers to the pH of the mixture of the second solution or slurry and the first solution or slurry while the second solution or slurry is mixed.

The time during which the pH of the mixture passes through the particular range is 1-70 seconds, preferably 4-65 seconds, more preferably 10-60 seconds, and further preferably 15-55 seconds. When the time during which the pH of the mixture passes through the particular range is less than 1 second, sufficient mixing is not achieved. When the time during which the pH of the mixture passes through the particular range is more than 70 seconds, bismuth, iron, and the like aggregate. Therefore, the acrylonitrile yield of the obtained catalyst decreases in either case.

The time during which the pH of the mixture passes through the particular range can be adjusted by the rate at which the second solution or slurry is dropped into the first solution or slurry.

The above solution or slurry comprising at least molybdenum preferably further comprises silica.

The ammoxidation catalyst produced by the production method in the present embodiment exhibits high acrylonitrile selectivity by having the above configuration. For this, the present inventors consider as follows.

An active site in an ammoxidation reaction is a molybdate composed of bismuth, but high acrylonitrile selectivity cannot be obtained with it only. It is considered that when a molybdate composed of bismuth is combined with a molybdate comprising iron and molybdates comprising other metals, the acrylonitrile selectivity improves. However, it is considered that in a slurry preparation method in which a solution or slurry comprising at least bismuth and iron is introduced into a solution or slurry comprising at least molybdenum, bismuth ions in the slurry precipitate and aggregate in the range of pH 2.0-4.0, through which the mixture passes, and that a precursor form less likely to form a complex oxide with other metals is taken.

It is considered that in a slurry preparation method in which a solution or slurry comprising at least molybdenum and silica is introduced into a solution or slurry comprising at least bismuth and iron the aggregation of iron in the slurry proceeds in the range of pH 0.5-0.7, through which the mixture passes, and that a precursor form less likely to form a complex oxide with other metals is taken.

As the support for the ammoxidation catalyst, silica is preferably used from the viewpoint of a small decrease in acrylonitrile selectivity and being able to greatly improve the wear resistance and particle strength of the catalyst.

As for the timing of adding silica in the first preparation method, silica is preferably mixed with the solution or slurry comprising at least molybdenum. At this time, silica may be introduced into the solution or slurry comprising molybdenum, or the solution or slurry comprising at least molybdenum may be introduced into silica. Then, the solution or slurry comprising at least bismuth and iron is preferably introduced into the solution or slurry comprising at least molybdenum and silica. At this time, the pH of the solution or slurry comprising at least molybdenum and silica changes from 5.5-7.0 to 0.1-1.9. At this time, the pH of the slurry passes through pH 2.0-4.0, which is considered as the isoelectric point of silica. At the isoelectric point, the silica particles aggregate nonuniformly, and the aggregates can be decomposition active sites, which decrease acrylonitrile selectivity.

As for the timing of adding silica in the second preparation method, silica is preferably mixed with the solution or slurry comprising at least molybdenum. At this time, silica may be introduced into the solution or slurry comprising molybdenum, or the solution or slurry comprising at least molybdenum may be introduced into silica. Then, the solution or slurry comprising at least molybdenum and silica is preferably introduced into the solution or slurry comprising at least bismuth and iron. At this time, the pH of the solution or slurry comprising at least bismuth and iron changes from 0.1-0.5 to 0.7-1.9.

In other words, it is considered that the acrylonitrile selectivity can be improved by suppressing the aggregation of bismuth or the aggregation of iron, and suppressing the aggregation of silica particles at the isoelectric point in the case of using silica, in the step of preparing a precursor slurry.

However, the mechanism of action described above is a presumption, and is not bounded thereto.

The method for producing an ammoxidation catalyst in the present embodiment will be described in more detail below.

(Composition)

An ammoxidation catalyst in the present embodiment comprises molybdenum, bismuth, and iron. Molybdenum plays roles as a propylene adsorption site and an ammonia activation site. In addition, bismuth plays the role of activating propylene and abstracting α-position hydrogen to produce a π allyl species. Further, iron plays the role of supplying oxygen present in a gas phase to catalytic active sites by trivalent/divalent redox.

In addition, optional components that may be contained in the ammoxidation catalyst produced in the present embodiment are not particularly limited. Examples of the optional components include one or more elements X selected from nickel, cobalt, magnesium, calcium, zinc, strontium, and barium, one or more elements Y selected from cerium, chromium, lanthanum, neodymium, yttrium, praseodymium, samarium, aluminum, gallium, and indium, and one or more elements Z selected from the group consisting of potassium, rubidium, and cesium. The element X plays the role of forming a molybdate having moderate lattice defects and smoothing the movement of oxygen in the bulk. The element Y can have a redox function in the catalyst like iron. Further, the element Z can play the role of suppressing the decomposition reactions of a main product and raw materials by blocking acid sites present on the catalyst surface.

The ammoxidation catalyst preferably has a composition represented by the following general formula (1). When the ammoxidation catalyst has such a composition, the acrylonitrile selectivity tends to improve more.

$$Mo_{12}Bi_aFe_bX_cY_dZ_eO_f \qquad (1)$$

wherein X represents one or more elements selected from nickel, cobalt, magnesium, calcium, zinc, strontium, and barium, Y represents one or more elements selected from cerium, chromium, lanthanum, neodymium, yttrium, praseodymium, samarium, aluminum, gallium, and indium, and Z represents one or more elements selected from potassium, rubidium, and cesium.

a represents the atomic ratio of bismuth to 12 atoms of molybdenum. $0.1 \leq a \leq 2.0$, preferably $0.15 \leq a \leq 1.0$, and more preferably $0.2 \leq a \leq 0.7$.

b represents the atomic ratio of iron to 12 atoms of molybdenum. $0.1 \leq b \leq 3.0$, preferably $0.5 \leq b \leq 2.5$, and more preferably $1.0 \leq b \leq 2.0$.

c represents the atomic ratio of X to 12 atoms of molybdenum. $0.1 \leq c \leq 10.0$, preferably $3.0 \leq c \leq 9.0$, and more preferably $5.0 \leq c \leq 8.5$.

d represents the atomic ratio of Y to 12 atoms of molybdenum. $0.1 \leq d \leq 3.0$, preferably $0.2 \leq d \leq 2.0$, and more preferably $0.3 \leq d \leq 1.5$.

e represents the atomic ratio of Z to 12 atoms of molybdenum. $0.01 \leq e \leq 2.0$, and preferably $0.05 \leq e \leq 1.0$.

f represents the atomic ratio of oxygen to 12 atoms of molybdenum and is the number of atoms of oxygen necessary to satisfy the valence requirements of other elements present.

When acrylonitrile is industrially produced, a fluidized bed reaction in which a catalyst is flowed by a reaction gas is generally selected. Therefore, the ammoxidation catalyst preferably has a certain strength or more. From such a viewpoint, the ammoxidation catalyst may be supported on a support. Examples of the support for the ammoxidation catalyst include oxides such as silica, alumina, titania, and zirconia. Among these, silica is suitable as the support from the viewpoint of a small decrease in acrylonitrile selectivity and being able to greatly improve the wear resistance and particle strength of the catalyst.

The content of the support is preferably 30-70% by mass, more preferably 35-65% by mass, based on the total mass of the ammoxidation catalyst and the support. When the content of the support is 30% by mass or more, the wear resistance and particle strength of the catalyst tend to improve more. When the content of the support is 70% by mass or less, the acrylonitrile selectivity tends to improve more.

The raw material of silica used as the support is not particularly limited, but a silica sol is preferred. The primary particle diameter of silica contained in a silica sol is not particularly limited, and silicas having different primary particle diameters may be mixed and used.

[Method for Producing Ammoxidation Catalyst]

The method for producing an ammoxidation catalyst in the present embodiment comprises the precursor slurry preparation step of preparing a precursor slurry comprising molybdenum, bismuth, and iron (step (i)), the drying step of spray-drying the precursor slurry to obtain dry particles (step (ii)), and the calcination step of calcining the dry particles (step (iii)).

[Step (i)]

The step (i) is the step of preparing a precursor slurry comprising molybdenum, bismuth, and iron. At this time, water, silica, and a carboxylic acid may be further mixed as needed. In the step (i), the precursor slurry can be obtained, for example, by the first preparation method in which a solution or slurry comprising at least bismuth and iron is introduced into a solution or slurry comprising at least molybdenum or the second preparation method in which a solution or slurry comprising at least molybdenum is introduced into a solution or slurry comprising at least bismuth and iron.

In the first preparation method in which a solution or slurry comprising at least bismuth and iron (an introduced solution or slurry is hereinafter also referred to as a "second solution") is introduced while a solution or slurry comprising at least molybdenum is stirred (a solution or slurry into which another solution or slurry is introduced is hereinafter also referred to as a "first solution"), in the step of mixing the second solution with the first solution, the time during which the pH of the mixture passes through the range of pH 2.0-4.0 (hereinafter also referred to as a "first range") when changing from 5.5-7.0 (the pH of the first solution before the second solution is mixed) to 0.1-1.9 (the pH of the mixture after the mixing of the second solution with the first solution is completed) is 1-70 seconds, preferably 4-65 seconds, more preferably 10-60 seconds, and further preferably 15-55 seconds. When the time during which the pH of the mixture passes through the first range is 70 seconds or less, the aggregation of silica and bismuth is suppressed, and a catalyst having a good acrylonitrile yield is obtained. When the time during which the pH of the mixture passes through the first range is 1 second or more, a sufficiently mixed precursor slurry can be formed.

On the other hand, in the second preparation method in which a solution or slurry comprising at least molybdenum is introduced while a solution or slurry comprising at least bismuth and iron is stirred, in the step of mixing the second solution with the first solution, the time during which the pH of the mixture passes through the range of pH 0.5-0.7 (hereinafter also referred to as a "second range") when changing from 0.1-0.5 to 0.7-1.9 is 1-70 seconds, preferably 4-65 seconds, more preferably 10-60 seconds, and further preferably 15-55 seconds. When the time during which the pH of the mixture passes through the second range is 70 seconds or less, the aggregation of iron is suppressed, and a catalyst having a good acrylonitrile yield is obtained. When the time during which the pH of the mixture passes through the second range is 1 second or more, a sufficiently mixed precursor slurry can be formed.

The time during which the pH of the mixture passes through the first range or the second range (hereinafter also collectively referred to as a "particular range") can be adjusted by the rate at which the second solution is dropped into the first solution. The liquid temperature when the first solution and the second solution are mixed is preferably 30-50° C., more preferably 35-45° C.

When the precursor slurry preparation scale increases, variations are likely to occur in places in a container for the value of the time during which the pH of the mixture passes through the above particular range. One reason why variations occur is, for example, that when a stirring apparatus is mounted in a container containing the first solution, it is difficult to set an apparatus for dropping the second solution at the same position in the plane as the above stirring apparatus because the two apparatuses physically interfere with each other. In order to decrease these variations, it is necessary to make the second solution introduction rate and introduction method, the stirring power, and the container shape suitable. It is considered that when the variations in the time during which the pH of the mixture passes through the above particular range decrease, the fine dispersion of metal particles and silica particles in the slurry is promoted, and the acrylonitrile selectivity of the catalyst improves.

The vertical positions of the measurement of the pH of the precursor slurry are set at a distance of ⅓A from the bottom surface of a stirring container when the height from the bottom surface to the liquid surface when the first solution is placed in the stirring container is A. The horizontal positions of the measurement of the pH of the precursor slurry are set at a plurality of positions including at least two places, the outermost peripheral position in the container nearest to and the outermost peripheral position in the container farthest from a position where the above second solution is added while the above second solution is mixed with the first solution from the position where the second solution is introduced. A case where the shape of the stirring container is cylindrical corresponds to Example 1 described later, and the positions shown in FIG. 2 are set. In a case where the shape of the bottom surface of the stirring container is a curved surface, for example, a spherical surface, "the bottom surface of the stirring container" described above is read as "the bottom point of the stirring container".

Here, the time during which the pH at the above nearest outermost peripheral position in the container passes through the particular range is a first time, and the time during which the pH at the above farthest outermost peripheral position in the container passes through the particular range is a second time.

FIG. 1 is a conceptual diagram showing differences in changes in pH between measurement positions in a container in the first preparation method. FIG. 1 shows that when the outermost peripheral position in the container nearest to a position where the above second solution or slurry is added is a measurement position 1, and the outermost peripheral position in the container farthest from the position where the above second solution or slurry is added is a measurement position 2, differences can occur in changes in pH at the measurement positions.

In a case where there are a plurality of second solution dropping positions and/or stirring positions, when the position where changes in pH are fastest and the position where changes in pH are slowest can be determined from geometric relationship, pH is measured at the positions. On the other hand, when the position where changes in pH are fastest and the position where changes in pH are slowest cannot be determined from geometric arrangement, a plurality of outermost peripheral positions in the container are sampled, and among them, the position where changes in pH are fastest and the position where changes in pH are slowest are determined.

When the volume of the precursor slurry is large, for example, 10 L or more, the ratio of the second time to the first time (second time/first time) is preferably 3 or less. When the value of the above ratio is more than 3 with the apparatuses adopted and under the conditions adopted, the above ratio can be decreased by one or more methods selected from the group consisting of increasing the stirring rate, decreasing the second liquid dropping rate, making the stirring blade large or using a plurality of stirring blades, and using a plurality of second solution dropping positions.

In other words, the method for producing an ammoxidation catalyst in the present embodiment encompasses a method for producing an ammoxidation catalyst, wherein the volume of the above precursor slurry is 10 L or more, the time during which the pH of the above mixture passes through the above particular range at the outermost peripheral position in a container nearest to a position where the above second solution or slurry is added while the above second solution or slurry is mixed is designated as a first time, the time during which the pH of the above mixture passes through the above particular range at the outermost peripheral position in the container farthest from the position where the above second solution or slurry is added while the above second solution or slurry is mixed is designated as a second time, the above first time is within the range of 1-70 seconds, and the ratio of the above second time to the above first time is 3 or less.

When the precursor slurry volume is less than 10 L, the first time may be defined as the time during which the pH of the mixture passes through the particular range if it can be confirmed that no large difference occurs between the first time and the second time.

When the second solution is introduced into the container, the number of introduction nozzles is not particularly limited. In addition, from the viewpoint of making changes in the pH of the slurry uniform, when the solution or slurry is introduced, the stirring power for mixing the slurry is preferably 0.02 kW/m$^3$ or more, more preferably 0.08 kW/m$^3$ or more. Further, from a similar viewpoint, as the stirring container, a container whose cross section is circular is preferred.

The raw materials of the components used for the preparation of the precursor slurry are preferably salts soluble in water or nitric acid. The raw materials of elements, molybdenum, bismuth, and iron, are not particularly limited. Examples of the raw materials include ammonium salts, nitrates, hydrochlorides, sulfates, organic acid salts, and inorganic salts soluble in water or nitric acid. Particularly, as the raw material of molybdenum, ammonium salts are preferred. As the raw materials of bismuth and iron, their nitrates are preferred. Nitrates are also preferred in that in addition to easy handling, they do not cause the remaining of chlorine, which occurs when hydrochlorides are used, or the remaining of sulfur, which occurs when sulfates are used. Specific examples of the raw materials of the components include ammonium paramolybdate, bismuth nitrate, and ferric nitrate.

As the silica raw material, a silica sol is preferred. A preferred concentration of a silica sol in a state of a raw material in which other components are not mixed is 10-50% by mass.

A carboxylic acid compound may be added to the precursor slurry as needed. A carboxylic acid is a typical coordinating organic compound and is considered to promote higher dispersion of metal components by bonding to the metal components. The carboxylic acid compound is not particularly limited, but polycarboxylic acids including dicarboxylic acids are preferred. Examples thereof include oxalic acid, tartaric acid, succinic acid, malic acid, and citric acid. Among these, oxalic acid and tartaric acid are preferred, and oxalic acid is more preferred.

[Step (ii)]

The step (ii) is the step of drying the precursor slurry for forming. The step (ii) is preferably the step of spray-drying the precursor slurry to obtain dry particles. By spray-drying the precursor slurry, spherical fine particles suitable for a fluidized bed reaction can be obtained. As the spray drying apparatus, general ones such as a rotating disk type and a nozzle type can be used. By adjusting the spray drying conditions, the particle diameter of the catalyst can be adjusted. When the catalyst is used as a fluidized bed catalyst, the particle diameter of the catalyst is preferably 25-180 μm. One example of conditions for obtaining catalyst particles having a preferred particle diameter include spray drying performed by using a centrifugal spraying apparatus equipped with a dish-shaped rotor mounted in the center of the upper portion of a dryer and maintaining the inlet air temperature of the dryer at 180-250° C. and the outlet temperature at 100-150° C.

[Step (iii)]

The step (iii) is the step of calcining the formed body such as dry particles obtained by the drying. The dry particles can contain nitric acid, and therefore denitration treatment is preferably performed before calcination. In the denitration treatment, heating at 150-450° C. for 1.5-3 hours is preferably performed. The calcination can be performed under an air atmosphere. The calcination temperature is preferably 550-650° C. When the calcination temperature is 550° C. or more, crystal growth proceeds sufficiently, and the acrylonitrile selectivity of the obtained catalyst tends to improve more. When the calcination temperature is 650° C. or less, the surface area of the obtained catalyst increases, and the reaction activity of propylene tends to improve more.

[Method for Producing Acrylonitrile]

A method for producing acrylonitrile in the present embodiment comprises the reaction step of reacting propylene, molecular oxygen, and ammonia in the presence of the above-described ammoxidation catalyst to produce acrylonitrile.

The production of acrylonitrile by an ammoxidation reaction can be carried out by a fixed bed reactor or a fluidized bed reactor. Of these, a fluidized bed reactor is preferred from the viewpoint of efficiently removing heat generated in the reaction and increasing the yield of acrylonitrile.

Propylene and ammonia that are raw materials of the ammoxidation reaction need not necessarily be of high purity, and those of industrial grades can be used. The molar ratio between propylene, ammonia, and oxygen (propylene/ammonia/oxygen) in a raw material gas is preferably 1.0/1.0-1.5/1.6-2.2.

The reaction temperature is preferably 380-480° C. The reaction pressure is preferably atmospheric pressure-0.3 MPa. The time of contact between the raw material gas and the catalyst is preferably 2-7 seconds, more preferably 3-6 seconds.

EXAMPLES

The present embodiment will be described in more detail below by giving Examples, but the present embodiment is not limited by the Examples described below. The values of catalyst compositions described in the Examples and the Comparative Examples are the same as those of the charge compositions of elements.

Example 1

A catalyst in which a metal oxide in which the composition of metal components was represented by $Mo_{12.00}Bi_{0.37}Fe_{1.53}Co_{4.11}Ni_{3.30}Ce_{0.81}Rb_{0.14}$ was supported on 40% by mass of silica was produced by the following procedure.

First, 25.0 g of oxalic acid dihydrate dissolved in 200 g of water was added to 1333 g of a silica sol comprising 30% by mass of $SiO_2$, and 481.9 g of ammonium paramolybdate $[(NH_4)_6Mo_7O_{24}\cdot 4H_2O]$ dissolved in 866.3 g of water was added under stirring to obtain a first solution comprising molybdenum and silica. The first solution was placed in a container having a volume of 5 liters with a stirring apparatus, and a pH recorder (DKK-TOA CORPORATION HM-30P) was mounted. The liquid temperature was adjusted at 40° C., and then the pH of the first solution was measured to find to be 5.72 (first pH).

Next, 41.1 g of bismuth nitrate $[Bi(NO_3)_3\cdot 5H_2O]$, 140.6 g of iron nitrate $[Fe(NO_3)_3\cdot 9H_2O]$, 272.3 g of cobalt nitrate $[Co(NO_3)_2\cdot 6H_2O]$, 218.2 g of nickel nitrate $[Ni(NO_3)_2\cdot 6H_2O]$, 80.3 g of cerium nitrate $[Ce(NO_3)_3\cdot 6H_2O]$, and 4.81 g of rubidium nitrate $[RbNO_3]$ were dissolved in 393.8 g of 16.6% by mass nitric acid to obtain a second solution, and the liquid temperature was adjusted at 40° C.

While the first solution was stirred by the stirring blade mounted in the center of the container, the second solution was mixed while being dropped at a rate of 49.5 g/sec, to obtain a slurry. The pH of the precursor slurry after the completion of the mixing was 1.02 (second pH). As a result of measurement by the pH recorder (DKK-TOA CORPORATION, HM-30P), at this time, the time during which the mixture at the outermost peripheral position in the container nearest to the position where the second solution was added passed through the range of pH 2.0 (fourth pH)-4.0 (third pH) was 5 seconds (first time). The time during which the mixture at the outermost peripheral position in the container farthest from the position where the second solution was added passed through the range of pH 2.0-4.0 was 5 seconds (second time). The volume of the precursor slurry was 3.1 L.

The plan view and side view of FIG. 2 schematically show the second solution dropping position and the pH measurement positions in the container. The measurement position 1 in FIG. 2 shows the outermost peripheral position in the container nearest to the position where the second solution is added, and the measurement position 2 shows the outermost peripheral position in the container farthest from the position where the second solution is added.

The obtained precursor slurry was dried using a rotating disk type spray dryer. At this time, the air temperature at the dryer inlet was 230° C., and the air temperature at the outlet was 110° C. The number of revolutions of the disk was set at 12500 revolutions/min.

The obtained dry body was maintained at 200° C. for 5 minutes, heated from 200° C. to 450° C. at 2.5° C./min, and maintained at 450° C. for 20 minutes for denitration. The obtained denitrated powder was calcined at 590° C. for 2 hours to obtain a catalyst.

Example 2

A catalyst was produced as in Example 1 except that the time during which the mixture at the outermost peripheral position in the container nearest to the position where the second solution was added passed through the range of pH 2.0-4.0 was 25 seconds, and the time during which the mixture at the outermost peripheral position in the container farthest from the position where the second solution was added passed through the range of pH 2.0-4.0 was 25 seconds. At this time, the rate at which the second solution was dropped into the first solution was 9.9 g/sec.

Example 3

A catalyst was produced as in Example 1 except that the time during which the mixture at the outermost peripheral position in the container nearest to the position where the second solution was added passed through the range of pH 2.0-4.0 was 45 seconds, and the time during which the mixture at the outermost peripheral position in the container farthest from the position where the second solution was added passed through the range of pH 2.0-4.0 was 45 seconds. At this time, the rate at which the second solution was dropped into the first solution was 5.5 g/sec.

Example 4

A catalyst was produced as in Example 1 except that the time during which the mixture at the outermost peripheral position in the container nearest to the position where the second solution was added passed through the range of pH 2.0-4.0 was 65 seconds, and the time during which the mixture at the outermost peripheral position in the container farthest from the position where the second solution was added passed through the range of pH 2.0-4.0 was 65 seconds. At this time, the rate at which the second solution was dropped into the first solution was 3.8 g/sec.

Example 5

A catalyst in which a metal oxide in which the composition of metal components was represented by $Mo_{12.00}Bi_{0.39}Fe_{1.60}Ni_{6.97}Mg_{0.77}Ce_{0.63}Rb_{0.17}$ was supported on 40% by mass of silica was produced by the following procedure.

First, 25.0 g of oxalic acid dihydrate dissolved in 200 g of water was added to 1333 g of a silica sol comprising 30% by mass of $SiO_2$, and 485.9 g of ammonium paramolybdate $[(NH_4)_6Mo_7O_{24}\cdot 4H_2O]$ dissolved in 873.5 g of water was added under stirring to obtain a first solution comprising molybdenum and silica. The liquid temperature was adjusted at 40° C., and then the pH of the first solution was measured as in Example 1 to find to be 5.76.

Next, 43.1 g of bismuth nitrate $[Bi(NO_3)_3\cdot 5H_2O]$, 148.0 g of iron nitrate $[Fe(NO_3)_3\cdot 9H_2O]$, 464.7 g of nickel nitrate $[Ni(NO_3)_2\cdot 6H_2O]$, 45.5 g of magnesium nitrate $[Mg(NO_3)_2\cdot 6H_2O]$, 62.6 g of cerium nitrate $[Ce(NO_3)_3\cdot 6H_2O]$, and 5.89 g of rubidium nitrate $[RbNO_3]$ were dissolved in 396.7 g of 16.6% by mass nitric acid to obtain a second solution, and the second solution was adjusted at a liquid temperature of 40° C.

The second solution was mixed with the first solution while being dropped at a rate of 49.5 g/sec, to obtain a slurry. The pH of the precursor slurry after the completion of the mixing was 1.04. As a result of measurement by a pH recorder (DKK-TOA CORPORATION, HM-30P), at this time, the time during which the mixture at the outermost peripheral position in the container nearest to the position where the second solution was added passed through the range of pH 2.0-4.0 was 5 seconds. The time during which the mixture at the outermost peripheral position in the container farthest from the position where the second solution was added passed through the range of pH 2.0-4.0 was 5 seconds. The volume of the precursor slurry was 3.1 L.

The obtained precursor slurry was dried using a rotating disk type spray dryer. At this time, the air temperature at the dryer inlet was 230° C., and the air temperature at the outlet was 110° C. The number of revolutions of the disk was set at 12500 revolutions/min.

The obtained dry body was maintained at 200° C. for 5 minutes, heated from 200° C. to 450° C. at 2.5° C./min, and maintained at 450° C. for 20 minutes for denitration. The obtained denitrated powder was calcined at 580° C. for 2 hours to obtain a catalyst.

Example 6

A catalyst was produced as in Example 5 except that the time during which the mixture at the outermost peripheral position in the container nearest to the position where the second solution was added passed through the range of pH 2.0-4.0 was 25 seconds, and the time during which the mixture at the outermost peripheral position in the container farthest from the position where the second solution was added passed through the range of pH 2.0-4.0 was 25 seconds. At this time, the rate at which the second solution was dropped into the first solution was 9.9 g/sec.

Example 7

A catalyst was produced as in Example 5 except that the time during which the mixture at the outermost peripheral position in the container nearest to the position where the second solution was added passed through the range of pH 2.0-4.0 was 45 seconds, and the time during which the mixture at the outermost peripheral position in the container farthest from the position where the second solution was added passed through the range of pH 2.0-4.0 was 45 seconds. At this time, the rate at which the second solution was dropped into the first solution was 5.5 g/sec.

Example 8

A catalyst was produced as in Example 5 except that the time during which the mixture at the outermost peripheral position in the container nearest to the position where the second solution was added passed through the range of pH 2.0-4.0 was 65 seconds, and the time during which the mixture at the outermost peripheral position in the container farthest from the position where the second solution was added passed through the range of pH 2.0-4.0 was 65 seconds. At this time, the rate at which the second solution was dropped into the first solution was 3.8 g/sec.

Example 9

A catalyst in which a metal oxide in which the composition of metal components was represented by $Mo_{12.00}Bi_{0.34}Fe_{1.60}Co_{4.30}Ni_{3.45}Ce_{0.68}Rb_{0.16}$ was supported on 42% by mass of silica was produced by the following procedure.

First, 25.0 g of oxalic acid dihydrate dissolved in 200 g of water was added to 1400 g of a silica sol comprising 30% by mass of $SiO_2$, and 465.5 g of ammonium paramolybdate $[(NH_4)_6Mo_7O_{24}\cdot 4H_2O]$ dissolved in 836.85 g of water was added under stirring to obtain a first solution comprising molybdenum and silica. The liquid temperature was adjusted at 40° C., and then the pH of the first solution was measured as in Example 1 to find to be 5.81.

Next, 36.1 g of bismuth nitrate $[Bi(NO_3)_3\cdot 5H_2O]$, 141.6 g of iron nitrate $[Fe(NO_3)_3\cdot 9H_2O]$, 275.1 g of cobalt nitrate $[Co(NO_3)_2\cdot 6H_2O]$, 219.9 g of nickel nitrate $[Ni(NO_3)_2\cdot 6H_2O]$, 64.6 g of cerium nitrate $[Ce(NO_3)_3\cdot 6H_2O]$, and 5.33 g of rubidium nitrate $[RbNO_3]$ were dissolved in 394.5 g of 16.6% by mass nitric acid to obtain a second solution, and the liquid temperature was adjusted at 40° C.

The second solution was mixed with the first solution while being dropped at a rate of 49.5 g/sec, to obtain a slurry. The pH of the precursor slurry after the completion of the mixing was 1.05. As a result of measurement by a pH recorder (DKK-TOA CORPORATION, HM-30P), at this time, the time during which the mixture at the outermost peripheral position in the container nearest to the position where the second solution was added passed through the range of pH 2.0-4.0 was 5 seconds. The time during which the mixture at the outermost peripheral position in the container farthest from the position where the second solution was added passed through the range of pH 2.0-4.0 was 5 seconds. The volume of the precursor slurry was 3.1 L.

The obtained precursor slurry was dried using a rotating disk type spray dryer. At this time, the air temperature at the dryer inlet was 230° C., and the air temperature at the outlet was 110° C. The number of revolutions of the disk was set at 12500 revolutions/min.

The obtained dry body was maintained at 200° C. for 5 minutes, heated from 200° C. to 450° C. at 2.5° C./min, and maintained at 450° C. for 20 minutes for denitration. The obtained denitrated powder was calcined at 585° C. for 2 hours to obtain a catalyst.

Example 10

A catalyst was produced as in Example 9 except that the time during which the mixture at the outermost peripheral position in the container nearest to the position where the second solution was added passed through the range of pH 2.0-4.0 was 45 seconds, and the time during which the mixture at the outermost peripheral position in the container farthest from the position where the second solution was added passed through the range of pH 2.0-4.0 was 45 seconds. At this time, the rate at which the second solution was dropped into the first solution was 5.5 g/sec.

Example 11

A catalyst was produced as in Example 9 except that the time during which the mixture at the outermost peripheral position in the container nearest to the position where the second solution was added passed through the range of pH 2.0-4.0 was 1.5 seconds, and the time during which the mixture at the outermost peripheral position in the container farthest from the position where the second solution was added passed through the range of pH 2.0-4.0 was 1.5 seconds. At this time, the rate at which the second solution was dropped into the first solution was 165 g/sec.

Example 12

A catalyst in which a metal oxide in which the composition of metal components was represented by $Mo_{12.00}Bi_{0.57}Fe_{1.01}Co_{6.83}Ni_{0.98}Mg_{0.98}Ce_{0.38}Rb_{0.12}$ was supported on 40% by mass of silica was produced by the following procedure.

First, 25.0 g of oxalic acid dihydrate dissolved in 200 g of water was added to 1333 g of a silica sol comprising 30% by mass of $SiO_2$, and 482.0 g of ammonium paramolybdate $[(NH_4)_6Mo_7O_{24}\cdot 4H_2O]$ dissolved in 866.4 g of water was added under stirring to obtain a first solution comprising molybdenum and silica. The liquid temperature was adjusted at 40° C., and then the pH of the first solution was measured as in Example 1 to find to be 5.83.

Next, 62.7 g of bismuth nitrate $[Bi(NO_3)_3\cdot 5H_2O]$, 93.0 g of iron nitrate $[Fe(NO_3)_3\cdot 9H_2O]$, 452.3 g of cobalt nitrate $[Co(NO_3)_2\cdot 6H_2O]$, 64.5 g of nickel nitrate $[Ni(NO_3)_2\cdot 6H_2O]$, 56.9 g of magnesium nitrate $[Mg(NO_3)_2\cdot 6H_2O]$, 37.4 g of cerium nitrate $[Ce(NO_3)_3\cdot 6H_2O]$, and 3.93 g of rubidium nitrate $[RbNO_3]$ were dissolved in 395.2 g of 16.6% by mass nitric acid to obtain a second solution, and the liquid temperature was adjusted at 40° C.

The second solution was mixed with the first solution while being dropped at a rate of 5.5 g/sec, to obtain a slurry. The pH of the precursor slurry after the completion of the mixing was 1.01. As a result of measurement by a pH recorder (DKK-TOA CORPORATION, HM-30P), at this time, the time during which the mixture at the outermost peripheral position in the container nearest to the position where the second solution was added passed through the range of pH 2.0-4.0 was 45 seconds. The time during which the mixture at the outermost peripheral position in the container farthest from the position where the second solution was added passed through the range of pH 2.0-4.0 was 45 seconds. The volume of the precursor slurry was 3.1 L.

The obtained precursor slurry was dried using a rotating disk type spray dryer. At this time, the air temperature at the dryer inlet was 230° C., and the air temperature at the outlet was 110° C. The number of revolutions of the disk was set at 12500 revolutions/min.

The obtained dry body was maintained at 200° C. for 5 minutes, heated from 200° C. to 450° C. at 2.5° C./min, and maintained at 450° C. for 20 minutes for denitration. The obtained denitrated powder was calcined at 590° C. for 2 hours to obtain a catalyst.

Example 13

A catalyst in which a metal oxide in which the composition of metal components was represented by $Mo_{12.00}Bi_{0.57}Fe_{1.01}Co_{2.24}Ni_{6.54}Ce_{0.38}Rb_{0.12}$ was supported on 40% by mass of silica was produced by the following procedure.

First, 25.0 g of oxalic acid dihydrate dissolved in 200 g of water was added to 1333 g of a silica sol comprising 30% by mass of $SiO_2$, and 479.5 g of ammonium paramolybdate $[(NH_4)_6Mo_7O_{24}\cdot 4H_2O]$ dissolved in 855.9 g of water was added under stirring to obtain a first solution comprising molybdenum and silica. The liquid temperature was adjusted at 40° C., and then the pH of the first solution was measured as in Example 1 to find to be 5.75.

Next, 61.9 g of bismuth nitrate $[Bi(NO_3)_3\cdot 5H_2O]$, 91.9 g of iron nitrate $[Fe(NO_3)_3\cdot 9H_2O]$, 146.8 g of cobalt nitrate $[Co(NO_3)_2\cdot 6H_2O]$, 427.2 g of nickel nitrate $[Ni(NO_3)_2\cdot 6H_2O]$, 36.9 g of cerium nitrate $[Ce(NO_3)_3\cdot 6H_2O]$, and 3.88 g of rubidium nitrate $[RbNO_3]$ were dissolved in 393.2 g of 16.6% by mass nitric acid to obtain a second solution, and the liquid temperature was adjusted at 40° C.

The second solution was mixed with the first solution while being dropped at a rate of 5.5 g/sec, to obtain a slurry. The pH of the precursor slurry after the completion of the mixing was 0.99. As a result of measurement by a pH recorder (DKK-TOA CORPORATION, HM-30P), at this time, the time during which the mixture at the outermost peripheral position in the container nearest to the position where the second solution was added passed through the range of pH 2.0-4.0 was 45 seconds. The time during which the mixture at the outermost peripheral position in the container farthest from the position where the second solution was added passed through the range of pH 2.0-4.0 was 45 seconds. The volume of the precursor slurry was 3.1 L.

The obtained precursor slurry was dried using a rotating disk type spray dryer. At this time, the air temperature at the dryer inlet was 230° C., and the air temperature at the outlet was 110° C. The number of revolutions of the disk was set at 12500 revolutions/min.

The obtained dry body was maintained at 200° C. for 5 minutes, heated from 200° C. to 450° C. at 2.5° C./min, and maintained at 450° C. for 20 minutes for denitration. The obtained denitrated powder was calcined at 600° C. for 2 hours to obtain a catalyst.

Example 14

A catalyst in which a metal oxide in which the composition of metal components was represented by $Mo_{12.00}Bi_{0.82}Fe_{1.45}Co_{8.14}Ce_{0.55}Rb_{0.13}$ was supported on 40% by mass of silica was produced by the following procedure.

First, 25.0 g of oxalic acid dihydrate dissolved in 200 g of water was added to 1333 g of a silica sol comprising 30% by mass of $SiO_2$, and 462.7 g of ammonium paramolybdate $[(NH_4)_6Mo_7O_{24}\cdot 4H_2O]$ dissolved in 855.9 g of water was added under stirring to obtain a first solution comprising molybdenum and silica. The liquid temperature was adjusted at 40° C., and then the pH of the first solution was measured as in Example 1 to find to be 5.70.

Next, 88.5 g of bismuth nitrate [$Bi(NO_3)_3 \cdot 5H_2O$], 128.2 g of iron nitrate [$Fe(NO_3)_3 \cdot 9H_2O$], 517.3 g of cobalt nitrate [$Co(NO_3)_2 \cdot 6H_2O$], 52.4 g of cerium nitrate [$Ce(NO_3)_3 \cdot 6H_2O$], and 4.06 g of rubidium nitrate [$RbNO_3$] were dissolved in 391.1 g of 16.6% by mass nitric acid to obtain a second solution, and the liquid temperature was adjusted at 40° C.

The second solution was mixed with the first solution while being dropped at a rate of 5.5 g/sec, to obtain a slurry. The pH of the precursor slurry after the completion of the mixing was 1.04. As a result of measurement by a pH recorder (DKK-TOA CORPORATION, HM-30P), at this time, the time during which the mixture at the outermost peripheral position in the container nearest to the position where the second solution was added passed through the range of pH 2.0-4.0 was 45 seconds. The time during which the mixture at the outermost peripheral position in the container farthest from the position where the second solution was added passed through the range of pH 2.0-4.0 was 45 seconds. The volume of the precursor slurry was 3.1 L.

The obtained precursor slurry was dried using a rotating disk type spray dryer. At this time, the air temperature at the dryer inlet was 230° C., and the air temperature at the outlet was 110° C. The number of revolutions of the disk was set at 12500 revolutions/min.

The obtained dry body was maintained at 200° C. for 5 minutes, heated from 200° C. to 450° C. at 2.5° C./min, and maintained at 450° C. for 20 minutes for denitration. The obtained denitrated powder was calcined at 585° C. for 2 hours to obtain a catalyst.

Example 15

A catalyst in which a metal oxide in which the composition of metal components was represented by $Mo_{12.0}Bi_{1.05}Fe_{1.40}Co_{8.15}Ce_{0.70}Rb_{0.13}$ was supported on 40% by mass of silica was produced by the following procedure.

First, 25.0 g of oxalic acid dihydrate dissolved in 200 g of water was added to 1333 g of a silica sol comprising 30% by mass of $SiO_2$, and 450.8 g of ammonium paramolybdate [$(NH_4)_6Mo_7O_{24} \cdot 4H_2O$] dissolved in 810.3 g of water was added under stirring to obtain a first solution comprising molybdenum and silica. The liquid temperature was adjusted at 40° C., and then the pH of the first solution was measured as in Example 1 to find to be 5.74.

Next, 108.1 g of bismuth nitrate [$Bi(NO_3)_3 \cdot 5H_2O$], 120.1 g of iron nitrate [$Fe(NO_3)_3 \cdot 9H_2O$], 504.7 g of cobalt nitrate [$Co(NO_3)_2 \cdot 6H_2O$], 64.5 g of cerium nitrate [$Ce(NO_3)_3 \cdot 6H_2O$], and 3.96 g of rubidium nitrate [$RbNO_3$] were dissolved in 388.6 g of 16.6% by mass nitric acid to obtain a second solution, and the liquid temperature was adjusted at 40° C.

The second solution was mixed with the first solution while being dropped at a rate of 5.5 g/sec, to obtain a slurry. The pH of the precursor slurry after the completion of the mixing was 1.04. As a result of measurement by a pH recorder (DKK-TOA CORPORATION, HM-30P), at this time, the time during which the mixture at the outermost peripheral position in the container nearest to the position where the second solution was added passed through the range of pH 2.0-4.0 was 45 seconds. The time during which the mixture at the outermost peripheral position in the container farthest from the position where the second solution was added passed through the range of pH 2.0-4.0 was 45 seconds. The volume of the precursor slurry was 3.1 L.

The obtained precursor slurry was dried using a rotating disk type spray dryer. At this time, the air temperature at the dryer inlet was 230° C., and the air temperature at the outlet was 110° C. The number of revolutions of the disk was set at 12500 revolutions/min.

The obtained dry body was maintained at 200° C. for 5 minutes, heated from 200° C. to 450° C. at 2.5° C./min, and maintained at 450° C. for 20 minutes for denitration. The obtained denitrated powder was calcined at 585° C. for 2 hours to obtain a catalyst.

Example 16

A catalyst in which a metal oxide in which the composition of metal components was represented by $Mo_{12.00}Bi_{0.84}Fe_{2.06}Co_{6.67}Ce_{0.56}Rb_{0.12}$ was supported on 40% by mass of silica was produced by the following procedure.

First, 25.0 g of oxalic acid dihydrate dissolved in 200 g of water was added to 1333 g of a silica sol comprising 30% by mass of $SiO_2$, and 472.5 g of ammonium paramolybdate [$(NH_4)_6Mo_7O_{24} \cdot 4H_2O$] dissolved in 849.4 g of water was added under stirring to obtain a first solution comprising molybdenum and silica. The liquid temperature was adjusted at 40° C., and then the pH of the first solution was measured as in Example 1 to find to be 5.80.

Next, 90.7 g of bismuth nitrate [$Bi(NO_3)_3 \cdot 5H_2O$], 185.4 g of iron nitrate [$Fe(NO_3)_3 \cdot 9H_2O$], 432.8 g of cobalt nitrate [$Co(NO_3)_2 \cdot 6H_2O$], 54.4 g of cerium nitrate [$Ce(NO_3)_3 \cdot 6H_2O$], and 3.96 g of rubidium nitrate [$RbNO_3$] were dissolved in 391.6 g of 16.6% by mass nitric acid to obtain a second solution, and the liquid temperature was adjusted at 40° C.

The second solution was mixed with the first solution while being dropped at a rate of 5.5 g/sec, to obtain a slurry. The pH of the precursor slurry after the completion of the mixing was 1.00. As a result of measurement by a pH recorder (DKK-TOA CORPORATION, HM-30P), at this time, the time during which the mixture at the outermost peripheral position in the container nearest to the position where the second solution was added passed through the range of pH 2.0-4.0 was 45 seconds. The time during which the mixture at the outermost peripheral position in the container farthest from the position where the second solution was added passed through the range of pH 2.0-4.0 was 45 seconds. The volume of the precursor slurry was 3.1 L.

The obtained precursor slurry was dried using a rotating disk type spray dryer. At this time, the air temperature at the dryer inlet was 230° C., and the air temperature at the outlet was 110° C. The number of revolutions of the disk was set at 12500 revolutions/min.

The obtained dry body was maintained at 200° C. for 5 minutes, heated from 200° C. to 450° C. at 2.5° C./min, and maintained at 450° C. for 20 minutes for denitration. The obtained denitrated powder was calcined at 580° C. for 2 hours to obtain a catalyst.

Example 17

A catalyst in which a metal oxide in which the composition of metal components was represented by $Mo_{12.00}Bi_{0.27}Fe_{0.95}Co_{9.64}Ce_{0.18}Rb_{0.13}$ was supported on 40% by mass of silica was produced by the following procedure.

First, 25.0 g of oxalic acid dihydrate dissolved in 200 g of water was added to 1333 g of a silica sol comprising 30% by mass of $SiO_2$, and 483.6 g of ammonium paramolybdate

[(NH$_4$)$_6$Mo$_7$O$_{24}$.4H$_2$O] dissolved in 869.3 g of water was added under stirring to obtain a first solution comprising molybdenum and silica. The liquid temperature was adjusted at 40° C., and then the pH of the first solution was measured as in Example 1 to find to be 5.80.

Next, 29.4 g of bismuth nitrate [Bi(NO$_3$)$_3$.5H$_2$O], 88.0 g of iron nitrate [Fe(NO$_3$)$_3$.9H$_2$O], 640.5 g of cobalt nitrate [Co(NO$_3$)$_2$.6H$_2$O], 17.5 g of cerium nitrate [Ce(NO$_3$)$_3$.6H$_2$O], and 4.31 g of rubidium nitrate [RbNO$_3$] were dissolved in 396.7 g of 16.6% by mass nitric acid to obtain a second solution, and the liquid temperature was adjusted at 40° C.

The second solution was mixed with the first solution while being dropped at a rate of 5.5 g/sec, to obtain a slurry. The pH of the precursor slurry after the completion of the mixing was 0.98. As a result of measurement by a pH recorder (DKK-TOA CORPORATION, HM-30P), at this time, the time during which the mixture at the outermost peripheral position in the container nearest to the position where the second solution was added passed through the range of pH 2.0-4.0 was 45 seconds. The time during which the mixture at the outermost peripheral position in the container farthest from the position where the second solution was added passed through the range of pH 2.0-4.0 was 45 seconds. The volume of the precursor slurry was 3.1 L.

The obtained precursor slurry was dried using a rotating disk type spray dryer. At this time, the air temperature at the dryer inlet was 230° C., and the air temperature at the outlet was 110° C. The number of revolutions of the disk was set at 12500 revolutions/min.

The obtained dry body was maintained at 200° C. for 5 minutes, heated from 200° C. to 450° C. at 2.5° C./min, and maintained at 450° C. for 20 minutes for denitration. The obtained denitrated powder was calcined at 590° C. for 2 hours to obtain a catalyst.

Example 18

A catalyst in which a metal oxide in which the composition of metal components was represented by Mo$_{12.00}$Bi$_{0.27}$Fe$_{0.95}$Co$_{8.16}$Ni$_{1.48}$Ce$_{0.18}$Rb$_{0.13}$ was supported on 40% by mass of silica was produced by the following procedure.

First, 25.0 g of oxalic acid dihydrate dissolved in 200 g of water was added to 1333 g of a silica sol comprising 30% by mass of SiO$_2$, and 483.7 g of ammonium paramolybdate [(NH$_4$)$_6$Mo$_7$O$_{24}$.4H$_2$O] dissolved in 869.4 g of water was added under stirring to obtain a first solution comprising molybdenum and silica. The liquid temperature was adjusted at 40° C., and then the pH of the first solution was measured as in Example 1 to find to be 5.77.

Next, 29.4 g of bismuth nitrate [Bi(NO$_3$)$_3$.5H$_2$O], 88.0 g of iron nitrate [Fe(NO$_3$)$_3$.9H$_2$O], 542.5 g of cobalt nitrate [Co(NO$_3$)$_2$.6H$_2$O], 98.0 g of nickel nitrate [Ni(NO$_3$)$_2$.6H$_2$O], 17.6 g of cerium nitrate [Ce(NO$_3$)$_3$.6H$_2$O], and 4.31 g of rubidium nitrate [RbNO$_3$] were dissolved in 396.7 g of 16.6% by mass nitric acid to obtain a second solution, and the liquid temperature was adjusted at 40° C.

The second solution was mixed with the first solution while being dropped at a rate of 5.5 g/sec, to obtain a slurry. The pH of the precursor slurry after the completion of the mixing was 0.95. As a result of measurement by a pH recorder (DKK-TOA CORPORATION, HM-30P), at this time, the time during which the mixture at the outermost peripheral position in the container nearest to the position where the second solution was added passed through the range of pH 2.0-4.0 was 45 seconds. The time during which the mixture at the outermost peripheral position in the container farthest from the position where the second solution was added passed through the range of pH 2.0-4.0 was 45 seconds. The volume of the precursor slurry was 3.1 L.

The obtained precursor slurry was dried using a rotating disk type spray dryer. At this time, the air temperature at the dryer inlet was 230° C., and the air temperature at the outlet was 110° C. The number of revolutions of the disk was set at 12500 revolutions/min.

The obtained dry body was maintained at 200° C. for 5 minutes, heated from 200° C. to 450° C. at 2.5° C./min, and maintained at 450° C. for 20 minutes for denitration. The obtained denitrated powder was calcined at 585° C. for 2 hours to obtain a catalyst.

Example 19

A catalyst in which a metal oxide in which the composition of metal components was represented by Mo$_{12.00}$Bi$_{0.27}$Fe$_{0.95}$Co$_{7.67}$Ni$_{1.97}$Ce$_{0.18}$Rb$_{0.13}$ was supported on 40% by mass of silica was produced by the following procedure.

First, 25.0 g of oxalic acid dihydrate dissolved in 200 g of water was added to 1333 g of a silica sol comprising 30% by mass of SiO$_2$, and 483.7 g of ammonium paramolybdate [(NH$_4$)$_6$Mo$_7$O$_{24}$.4H$_2$O] dissolved in 869.4 g of water was added under stirring to obtain a first solution comprising molybdenum and silica. The liquid temperature was adjusted at 40° C., and then the pH of the first solution was measured as in Example 1 to find to be 5.76.

Next, 29.4 g of bismuth nitrate [Bi(NO$_3$)$_3$.5H$_2$O], 88.0 g of iron nitrate [Fe(NO$_3$)$_3$.9H$_2$O], 509.9 g of cobalt nitrate [Co(NO$_3$)$_2$.6H$_2$O], 130.6 g of nickel nitrate [Ni(NO$_3$)$_2$.6H$_2$O], 17.6 g of cerium nitrate [Ce(NO$_3$)$_3$.6H$_2$O], and 4.31 g of rubidium nitrate [RbNO$_3$] were dissolved in 396.8 g of 16.6% by mass nitric acid to obtain a second solution, and the liquid temperature was adjusted at 40° C.

The second solution was mixed with the first solution while being dropped at a rate of 5.5 g/sec, to obtain a slurry. The pH of the precursor slurry after the completion of the mixing was 0.97. As a result of measurement by a pH recorder (DKK-TOA CORPORATION, HM-30P), at this time, the time during which the mixture at the outermost peripheral position in the container nearest to the position where the second solution was added passed through the range of pH 2.0-4.0 was 45 seconds. The time during which the mixture at the outermost peripheral position in the container farthest from the position where the second solution was added passed through the range of pH 2.0-4.0 was 45 seconds. The volume of the precursor slurry was 3.1 L.

The obtained precursor slurry was dried using a rotating disk type spray dryer. At this time, the air temperature at the dryer inlet was 230° C., and the air temperature at the outlet was 110° C. The number of revolutions of the disk was set at 12500 revolutions/min.

The obtained dry body was maintained at 200° C. for 5 minutes, heated from 200° C. to 450° C. at 2.5° C./min, and maintained at 450° C. for 20 minutes for denitration. The obtained denitrated powder was calcined at 590° C. for 2 hours to obtain a catalyst.

Example 20

A catalyst in which a metal oxide in which the composition of metal components was represented by $Mo_{12.00}Bi_{0.27}Fe_{0.95}Co_{6.69}Ni_{2.9}Ce_{0.18}Rb_{0.13}$ was supported on 40% by mass of silica was produced by the following procedure.

First, 25.0 g of oxalic acid dihydrate dissolved in 200 g of water was added to 1333 g of a silica sol comprising 30% by mass of $SiO_2$, and 483.7 g of ammonium paramolybdate $[(NH_4)_6Mo_7O_{24}\cdot4H_2O]$ dissolved in 869.5 g of water was added under stirring to obtain a first solution comprising molybdenum and silica. The liquid temperature was adjusted at 40° C., and then the pH of the first solution was measured as in Example 1 to find to be 5.78.

Next, 29.4 g of bismuth nitrate $[Bi(NO_3)_3\cdot5H_2O]$, 88.0 g of iron nitrate $[Fe(NO_3)_3\cdot9H_2O]$, 444.5 g of cobalt nitrate $[Co(NO_3)_2\cdot6H_2O]$, 195.9 g of nickel nitrate $[Ni(NO_3)_2\cdot6H_2O]$, 17.6 g of cerium nitrate $[Ce(NO_3)_3\cdot6H_2O]$, and 4.31 g of rubidium nitrate $[RbNO_3]$ were dissolved in 396.8 g of 16.6% by mass nitric acid to obtain a second solution, and the liquid temperature was adjusted at 40° C.

The second solution was mixed with the first solution while being dropped at a rate of 5.5 g/sec, to obtain a slurry. The pH of the precursor slurry after the completion of the mixing was 1.05. As a result of measurement by a pH recorder (DKK-TOA CORPORATION, HM-30P), at this time, the time during which the mixture at the outermost peripheral position in the container nearest to the position where the second solution was added passed through the range of pH 2.0-4.0 was 45 seconds. The time during which the mixture at the outermost peripheral position in the container farthest from the position where the second solution was added passed through the range of pH 2.0-4.0 was 45 seconds. The volume of the precursor slurry was 3.1 L.

The obtained precursor slurry was dried using a rotating disk type spray dryer. At this time, the air temperature at the dryer inlet was 230° C., and the air temperature at the outlet was 110° C. The number of revolutions of the disk was set at 12500 revolutions/min.

The obtained dry body was maintained at 200° C. for 5 minutes, heated from 200° C. to 450° C. at 2.5° C./min, and maintained at 450° C. for 20 minutes for denitration. The obtained denitrated powder was calcined at 595° C. for 2 hours to obtain a catalyst.

Example 21

A catalyst in which a metal oxide in which the composition of metal components was represented by $Mo_{12.00}Bi_{0.34}Fe_{1.60}Co_{4.30}Ni_{3.45}Ce_{0.68}Rb_{0.16}$ was supported on 42% by mass of silica was produced by the following procedure.

First, 100.0 g of oxalic acid dihydrate dissolved in 800 g of water was added to 5333 g of a silica sol comprising 30% by mass of $SiO_2$, and 1925.6 g of ammonium paramolybdate $[(NH_4)_6Mo_7O_{24}\cdot4H_2O]$ dissolved in 3461.3 g of water was added under stirring to obtain a first solution comprising molybdenum and silica. The first solution was placed in a container having a volume of 20 liters with a stirring apparatus, and a pH recorder (DKK-TOA CORPORATION HM-30P) was mounted. The liquid temperature was adjusted at 40° C., and then the pH of the first solution was measured to find to be 5.80.

Next, 149.9 g of bismuth nitrate $[Bi(NO_3)_3\cdot5H_2O]$, 587.5 g of iron nitrate $[Fe(NO_3)_3\cdot9H_2O]$, 1137.7 g of cobalt nitrate $[Co(NO_3)_2\cdot6H_2O]$, 911.9 g of nickel nitrate $[Ni(NO_3)_2\cdot6H_2O]$, 268.4 g of cerium nitrate $[Ce(NO_3)_3\cdot6H_2O]$, and 21.4 g of rubidium nitrate $[RbNO_3]$ were dissolved in 1579.1 g of 16.6% by mass nitric acid to obtain a second solution, and the liquid temperature was adjusted at 40° C.

The second solution was mixed with the first solution while being dropped at a rate of 16.5 g/sec, to obtain a slurry. The stirring power during the mixing was set to be 0.3 $kW/m^3$ at the point of time when the dropping of the second solution was completed. The pH of the precursor slurry after the completion of the mixing was 1.00. As a result of measurement by a pH recorder (DKK-TOA CORPORATION, HM-30P), at this time, the time during which the mixture at the outermost peripheral position in the container nearest to the position where the second solution was added passed through the range of pH 2.0-4.0 was 60 seconds. The time during which the mixture at the outermost peripheral position in the container farthest from the position where the second solution was added passed through the range of pH 2.0-4.0 was 90 seconds. The volume of the precursor slurry was 12.1 L.

The obtained precursor slurry was dried using a rotating disk type spray dryer. At this time, the air temperature at the dryer inlet was 230° C., and the air temperature at the outlet was 110° C. The number of revolutions of the disk was set at 12500 revolutions/min.

The obtained dry body was maintained at 200° C. for 5 minutes, heated from 200° C. to 450° C. at 2.5° C./min, and maintained at 450° C. for 20 minutes for denitration. The obtained denitrated powder was calcined at 585° C. for 2 hours to obtain a catalyst.

Example 22

A catalyst was produced as in Example 21 except that the stirring power during the mixing was 0.06 $kW/m^3$, the time during which the mixture at the outermost peripheral position in the container nearest to the position where the second solution was added passed through the range of pH 2.0-4.0 was 60 seconds, and the time during which the mixture at the outermost peripheral position in the container farthest from the position where the second solution was added passed through the range of pH 2.0-4.0 was 192 seconds.

Comparative Example 1

A catalyst was produced as in Example 1 except that the time during which the mixture at the outermost peripheral position in the container nearest to the position where the second solution was added passed through the range of pH 2.0-4.0 was 110 seconds, and the time during which the mixture at the outermost peripheral position in the container farthest from the position where the second solution was added passed through the range of pH 2.0-4.0 was 110 seconds. At this time, the rate at which the second solution was dropped into the first solution was 2.6 g/sec.

Comparative Example 2

A catalyst was produced as in Example 5 except that the time during which the mixture at the outermost peripheral position in the container nearest to the position where the second solution was added passed through the range of pH 2.0-4.0 was 110 seconds, and the time during which the mixture at the outermost peripheral position in the container farthest from the position where the second solution was added passed through the range of pH 2.0-4.0 was 110 seconds. At this time, the rate at which the second solution was dropped into the first solution was 2.6 g/sec.

Comparative Example 3

A catalyst was produced as in Example 9 except that the time during which the mixture at the outermost peripheral position in the container nearest to the position where the second solution was added passed through the range of pH 2.0-4.0 was 110 seconds, and the time during which the mixture at the outermost peripheral position in the container farthest from the position where the second solution was added passed through the range of pH 2.0-4.0 was 110 seconds. At this time, the rate at which the second solution was dropped into the first solution was 2.6 g/sec.

Comparative Example 4

A catalyst was produced as in Example 9 except that the time during which the mixture at the outermost peripheral position in the container nearest to the position where the second solution was added passed through the range of pH 2.0-4.0 was 0.5 seconds, and the time during which the mixture at the outermost peripheral position in the container farthest from the position where the second solution was added passed through the range of pH 2.0-4.0 was 0.5 seconds. At this time, the rate at which the second solution was dropped into the first solution was 495 g/sec.

Comparative Example 5

A catalyst was produced as in Example 9 except that the time during which the mixture at the outermost peripheral position in the container nearest to the position where the second solution was added passed through the range of pH 2.0-4.0 was 80 seconds, and the time during which the mixture at the outermost peripheral position in the container farthest from the position where the second solution was added passed through the range of pH 2.0-4.0 was 80 seconds. At this time, the rate at which the second solution was dropped into the first solution was 3.1 g/sec.

Comparative Example 6

A catalyst was produced as in Example 12 except that the time during which the mixture at the outermost peripheral position in the container nearest to the position where the second solution was added passed through the range of pH 2.0-4.0 was 110 seconds, and the time during which the mixture at the outermost peripheral position in the container farthest from the position where the second solution was added passed through the range of pH 2.0-4.0 was 110 seconds. At this time, the rate at which the second solution was dropped into the first solution was 2.6 g/sec.

Comparative Example 7

A catalyst was produced as in Example 13 except that the time during which the mixture at the outermost peripheral position in the container nearest to the position where the second solution was added passed through the range of pH 2.0-4.0 was 110 seconds, and the time during which the mixture at the outermost peripheral position in the container farthest from the position where the second solution was added passed through the range of pH 2.0-4.0 was 110 seconds. At this time, the rate at which the second solution was dropped into the first solution was 2.6 g/sec.

Comparative Example 8

A catalyst was produced as in Example 14 except that the time during which the mixture at the outermost peripheral position in the container nearest to the position where the second solution was added passed through the range of pH 2.0-4.0 was 110 seconds, and the time during which the mixture at the outermost peripheral position in the container farthest from the position where the second solution was added passed through the range of pH 2.0-4.0 was 110 seconds. At this time, the rate at which the second solution was dropped into the first solution was 2.6 g/sec.

Comparative Example 9

A catalyst was produced as in Example 15 except that the time during which the mixture at the outermost peripheral position in the container nearest to the position where the second solution was added passed through the range of pH 2.0-4.0 was 110 seconds, and the time during which the mixture at the outermost peripheral position in the container farthest from the position where the second solution was added passed through the range of pH 2.0-4.0 was 110 seconds. At this time, the rate at which the second solution was dropped into the first solution was 2.6 g/sec.

Comparative Example 10

A catalyst was produced as in Example 16 except that the time during which the mixture at the outermost peripheral position in the container nearest to the position where the second solution was added passed through the range of pH 2.0-4.0 was 110 seconds, and the time during which the mixture at the outermost peripheral position in the container farthest from the position where the second solution was added passed through the range of pH 2.0-4.0 was 110 seconds. At this time, the rate at which the second solution was dropped into the first solution was 2.6 g/sec.

Comparative Example 11

A catalyst was produced as in Example 17 except that the time during which the mixture at the outermost peripheral position in the container nearest to the position where the second solution was added passed through the range of pH 2.0-4.0 was 110 seconds, and the time during which the mixture at the outermost peripheral position in the container farthest from the position where the second solution was added passed through the range of pH 2.0-4.0 was 110 seconds. At this time, the rate at which the second solution was dropped into the first solution was 2.6 g/sec.

Comparative Example 12

A catalyst was produced as in Example 18 except that the time during which the mixture at the outermost peripheral position in the container nearest to the position where the second solution was added passed through the range of pH 2.0-4.0 was 110 seconds, and the time during which the mixture at the outermost peripheral position in the container farthest from the position where the second solution was added passed through the range of pH 2.0-4.0 was 110 seconds. At this time, the rate at which the second solution was dropped into the first solution was 2.6 g/sec.

Comparative Example 13

A catalyst was produced as in Example 19 except that the time during which the mixture at the outermost peripheral position in the container nearest to the position where the second solution was added passed through the range of pH 2.0-4.0 was 110 seconds, and the time during which the mixture at the outermost peripheral position in the container farthest from the position where the second solution was added passed through the range of pH 2.0-4.0 was 110 seconds. At this time, the rate at which the second solution was dropped into the first solution was 2.6 g/sec.

Comparative Example 14

A catalyst was produced as in Example 20 except that the time during which the mixture at the outermost peripheral position in the container nearest to the position where the second solution was added passed through the range of pH 2.0-4.0 was 110 seconds, and the time during which the mixture at the outermost peripheral position in the container farthest from the position where the second solution was added passed through the range of pH 2.0-4.0 was 110 seconds. At this time, the rate at which the second solution was dropped into the first solution was 2.6 g/sec.

Comparative Example 15

A catalyst was produced as in Example 21 except that the time during which the mixture at the outermost peripheral position in the container nearest to the position where the second solution was added passed through the range of pH 2.0-4.0 was 110 seconds, and the time during which the mixture at the outermost peripheral position in the container farthest from the position where the second solution was added passed through the range of pH 2.0-4.0 was 143 seconds. At this time, the rate at which the second solution was dropped into the first solution was 9.0 g/sec.

The production conditions of the catalysts obtained in the Examples and the Comparative Examples are shown in Table 1.

[Ammoxidation Reaction Conditions and Results]

For a reaction tube used for the ammoxidation reaction of propylene, a Pyrex (registered trademark) glass tube having an inner diameter of 25 mm containing 16 10-mesh wire gauzes at intervals of 1 cm was used. An amount of a catalyst of 50 cc, a reaction temperature of 430° C., and a reaction pressure of 0.17 MPa were set, and a mixed gas (propylene, ammonia, oxygen, and helium) having a propylene volume of 9% was passed. The volume ratio of ammonia to propylene was set so that the sulfuric acid basic unit defined by the following formula was 20 kg/T-AN. The volume ratio of oxygen to propylene was set so that the oxygen concentration of the reactor outlet gas was 0.2±0.02% by volume. By changing the flow rate of the mixed gas, the contact time defined by the following formula can be changed. Thus, the propylene conversion rate defined by the following formula was set to be 99.3±0.2%. The yield of acrylonitrile produced by the reaction is defined as in the following formula.

$$\text{Sulfuric acid basic unit } (kg/T\text{-}AN) = \frac{\text{production weight } (T) \text{ of acrylonitrile}}{\text{weight (kg) of sulfuric acid necessary to neutralize unreacted ammonia}}$$

TABLE 1

| | | | | X | | | Y | Z | Time of passage through pH 2-4 (Seconds) | Slurry volume (L) | Second time/first time Ratio |
|---|---|---|---|---|---|---|---|---|---|---|---|
| | Mo | Bi | Fe | Co | Ni | Mg | Ce | Rb | | | |
| Example 1 | 12.00 | 0.37 | 1.53 | 4.11 | 3.30 | — | 0.81 | 0.14 | 5 | 3.1 | 1.0 |
| Example 2 | 12.00 | 0.37 | 1.53 | 4.11 | 3.30 | — | 0.81 | 0.14 | 25 | 3.1 | 1.0 |
| Example 3 | 12.00 | 0.37 | 1.53 | 4.11 | 3.30 | — | 0.81 | 0.14 | 45 | 3.1 | 1.0 |
| Example 4 | 12.00 | 0.37 | 1.53 | 4.11 | 3.30 | — | 0.81 | 0.14 | 65 | 3.1 | 1.0 |
| Example 5 | 12.00 | 0.39 | 1.60 | — | 6.97 | 0.77 | 0.63 | 0.17 | 5 | 3.1 | 1.0 |
| Example 6 | 12.00 | 0.39 | 1.60 | — | 6.97 | 0.77 | 0.63 | 0.17 | 25 | 3.1 | 1.0 |
| Example 7 | 12.00 | 0.39 | 1.60 | — | 6.97 | 0.77 | 0.63 | 0.17 | 45 | 3.1 | 1.0 |
| Example 8 | 12.00 | 0.39 | 1.60 | — | 6.97 | 0.77 | 0.63 | 0.17 | 65 | 3.1 | 1.0 |
| Example 9 | 12.00 | 0.34 | 1.60 | 4.30 | 3.45 | — | 0.68 | 0.16 | 5 | 3.1 | 1.0 |
| Example 10 | 12.00 | 0.34 | 1.60 | 4.30 | 3.45 | — | 0.68 | 0.16 | 45 | 3.1 | 1.0 |
| Example 11 | 12.00 | 0.34 | 1.60 | 4.30 | 3.45 | — | 0.68 | 0.16 | 1.5 | 3.1 | 1.0 |
| Example 12 | 12.00 | 0.57 | 1.01 | 6.83 | 0.98 | 0.98 | 0.38 | 0.12 | 45 | 3.1 | 1.0 |
| Example 13 | 12.00 | 0.57 | 1.01 | 2.24 | 6.54 | — | 0.38 | 0.12 | 45 | 3.1 | 1.0 |
| Example 14 | 12.00 | 0.82 | 1.45 | 8.14 | — | — | 0.55 | 0.13 | 45 | 3.1 | 1.0 |
| Example 15 | 12.00 | 1.05 | 1.40 | 8.15 | — | — | 0.70 | 0.13 | 45 | 3.1 | 1.0 |
| Example 16 | 12.00 | 0.84 | 2.06 | 6.67 | — | — | 0.56 | 0.12 | 45 | 3.1 | 1.0 |
| Example 17 | 12.00 | 0.27 | 0.95 | 9.64 | — | — | 0.18 | 0.13 | 45 | 3.1 | 1.0 |
| Example 18 | 12.00 | 0.27 | 0.95 | 8.16 | 1.48 | — | 0.18 | 0.13 | 45 | 3.1 | 1.0 |
| Example 19 | 12.00 | 0.27 | 0.95 | 7.67 | 1.97 | — | 0.18 | 0.13 | 45 | 3.1 | 1.0 |
| Example 20 | 12.00 | 0.27 | 0.95 | 6.69 | 2.95 | — | 0.18 | 0.13 | 45 | 3.1 | 1.0 |
| Example 21 | 12.00 | 0.34 | 1.60 | 4.30 | 3.45 | — | 0.68 | 0.16 | 60 | 12.1 | 1.5 |
| Example 22 | 12.00 | 0.34 | 1.60 | 4.30 | 3.45 | — | 0.68 | 0.16 | 60 | 12.1 | 3.2 |
| Comparative Example 1 | 12.00 | 0.37 | 1.53 | 4.11 | 3.30 | — | 0.81 | 0.14 | 110 | 3.1 | 1.0 |
| Comparative Example 2 | 12.00 | 0.39 | 1.60 | — | 6.97 | 0.77 | 0.63 | 0.17 | 110 | 3.1 | 1.0 |
| Comparative Example 3 | 12.00 | 0.34 | 1.60 | 4.30 | 3.45 | — | 0.68 | 0.16 | 110 | 3.1 | 1.0 |
| Comparative Example 4 | 12.00 | 0.34 | 1.60 | 4.30 | 3.45 | — | 0.68 | 0.16 | 0.5 | 3.1 | 1.0 |
| Comparative Example 5 | 12.00 | 0.34 | 1.60 | 4.30 | 3.45 | — | 0.68 | 0.16 | 80 | 3.1 | 1.0 |
| Comparative Example 6 | 12.00 | 0.57 | 1.01 | 6.83 | 0.98 | 0.98 | 0.38 | 0.12 | 110 | 3.1 | 1.0 |
| Comparative Example 7 | 12.00 | 0.57 | 1.01 | 2.24 | 6.54 | — | 0.38 | 0.12 | 110 | 3.1 | 1.0 |
| Comparative Example 8 | 12.00 | 0.82 | 1.45 | 8.14 | — | — | 0.55 | 0.13 | 110 | 3.1 | 1.0 |
| Comparative Example 9 | 12.00 | 1.05 | 1.40 | 8.15 | — | — | 0.70 | 0.13 | 110 | 3.1 | 1.0 |
| Comparative Example 10 | 12.00 | 0.84 | 2.06 | 6.67 | — | — | 0.56 | 0.12 | 110 | 3.1 | 1.0 |
| Comparative Example 11 | 12.00 | 0.27 | 0.95 | 9.64 | — | — | 0.18 | 0.13 | 110 | 3.1 | 1.0 |
| Comparative Example 12 | 12.00 | 0.27 | 0.95 | 8.16 | 1.48 | — | 0.18 | 0.13 | 110 | 3.1 | 1.0 |
| Comparative Example 13 | 12.00 | 0.27 | 0.95 | 7.67 | 1.97 | — | 0.18 | 0.13 | 110 | 3.1 | 1.0 |
| Comparative Example 14 | 12.00 | 0.27 | 0.95 | 6.69 | 2.95 | — | 0.18 | 0.13 | 110 | 3.1 | 1.0 |
| Comparative Example 15 | 12.00 | 0.34 | 1.60 | 4.30 | 3.45 | — | 0.68 | 0.16 | 110 | 12.1 | 1.3 |

-continued $$\text{Contact time (sec.)} = \frac{\text{amount of catalyst (cc)}}{\text{mixed gas flow rate (cc-}NTP\text{/sec.)}} \times$$

$$\frac{273}{273 + \text{reaction temperature (° C.)}} \times \frac{\text{reaction pressure (Mpa)}}{0.10}$$

$$\text{Propylene conversion rate (\%)} = \frac{\text{consumed propylene (mol)}}{\text{supplied propylene (mol)}} \times 100$$

$$\text{Acrylonitrile yield (\%)} = \frac{\text{produced acrylonitrile (mol)}}{\text{supplied acrylonitrile (mol)}} \times 100$$

Reaction conditions and reaction results for the catalysts obtained in the Examples and the Comparative Examples are shown in Table 2. The reaction time was 20 hours.

TABLE 2

|  | Ammonia/propylene Molar ratio | Oxygen/propylene Molar ratio | Contact time sec. | Propylene conversion rate % | AN yield % |
| --- | --- | --- | --- | --- | --- |
| Example 1 | 1.19 | 2.04 | 3.5 | 99.3 | 84.2 |
| Example 2 | 1.22 | 2.03 | 3.8 | 99.2 | 84.3 |
| Example 3 | 1.21 | 2.00 | 3.7 | 99.2 | 84.5 |
| Example 4 | 1.22 | 1.98 | 4.0 | 99.1 | 84.2 |
| Example 5 | 1.18 | 1.96 | 3.8 | 99.2 | 84.1 |
| Example 6 | 1.22 | 2.05 | 3.9 | 99.3 | 84.3 |
| Example 7 | 1.17 | 1.90 | 4.0 | 99.3 | 84.4 |
| Example 8 | 1.25 | 2.07 | 3.9 | 99.2 | 84.2 |
| Example 9 | 1.21 | 2.03 | 3.4 | 99.4 | 84.3 |
| Example 10 | 1.19 | 1.94 | 3.5 | 99.3 | 84.5 |
| Example 11 | 1.18 | 1.98 | 3.8 | 99.2 | 84.1 |
| Example 12 | 1.21 | 2.01 | 3.8 | 99.3 | 84.5 |
| Example 13 | 1.22 | 1.98 | 4.0 | 99.3 | 84.3 |
| Example 14 | 1.23 | 1.97 | 4.1 | 99.2 | 84.2 |
| Example 15 | 1.21 | 1.96 | 3.6 | 99.3 | 84.2 |
| Example 16 | 1.24 | 2.04 | 3.8 | 99.3 | 84.1 |
| Example 17 | 1.21 | 1.98 | 3.9 | 99.2 | 84.3 |
| Example 18 | 1.19 | 2.00 | 4.0 | 99.3 | 84.1 |
| Example 19 | 1.18 | 2.06 | 4.0 | 99.3 | 84.2 |
| Example 20 | 1.21 | 2.00 | 4.1 | 99.3 | 84.1 |
| Example 21 | 1.19 | 1.97 | 4.3 | 99.2 | 84.4 |
| Example 22 | 1.18 | 2.01 | 4.5 | 99.3 | 84.1 |
| Comparative Example 1 | 1.15 | 1.98 | 4.2 | 99.2 | 83.8 |
| Comparative Example 2 | 1.20 | 2.10 | 4.5 | 99.3 | 83.7 |
| Comparative Example 3 | 1.16 | 1.99 | 4.3 | 99.1 | 83.6 |
| Comparative Example 4 | 1.17 | 2.05 | 4.0 | 99.3 | 83.9 |
| Comparative Example 5 | 1.19 | 2.03 | 4.1 | 99.2 | 83.8 |
| Comparative Example 6 | 1.18 | 2.06 | 4.5 | 99.2 | 83.4 |
| Comparative Example 7 | 1.16 | 2.01 | 4.6 | 99.2 | 83.5 |
| Comparative Example 8 | 1.17 | 1.99 | 4.4 | 99.2 | 83.6 |
| Comparative Example 9 | 1.18 | 2.06 | 4.6 | 99.2 | 83.6 |
| Comparative Example 10 | 1.16 | 2.09 | 4.5 | 99.2 | 83.5 |
| Comparative Example 11 | 1.17 | 2.06 | 4.5 | 99.2 | 83.5 |
| Comparative Example 12 | 1.18 | 2.06 | 4.6 | 99.2 | 83.7 |
| Comparative Example 13 | 1.17 | 2.06 | 4.5 | 99.2 | 83.4 |
| Comparative Example 14 | 1.20 | 1.99 | 4.3 | 99.2 | 83.5 |
| Comparative Example 15 | 1.17 | 2.08 | 4.8 | 99.2 | 83.7 |

As shown in the above Table 1, in the ammoxidation reaction of propylene in which the catalysts produced by the present embodiment were used, acrylonitrile was obtained in good yields. In addition, it is seen that for the catalysts produced by the present embodiment, the propylene activity is high, and the contact time for obtaining the same conversion rate in the ammoxidation reaction of propylene is short.

INDUSTRIAL APPLICABILITY

The method for producing an ammoxidation catalyst according to the present invention has industrial applicability as a method for producing a catalyst used for the ammoxidation reaction of propylene.

The invention claimed is:
1. A method for producing an ammoxidation catalyst, comprising:
a step of preparing a precursor slurry that is a precursor of the catalyst;
a drying step of obtaining a dry particle from the precursor slurry; and
a calcination step of calcining the dry particle, wherein
the step of preparing the precursor slurry is a step of mixing a first solution or slurry having a first pH and a second solution or slurry to obtain a solution or slurry having a second pH after completion of mixing,
a time during which a pH of a mixture passes through a particular range having an upper limit and a lower limit while the second solution or slurry is mixed is 1-70 seconds, the upper limit and the lower limit being designated as a third pH and a fourth pH respectively, and
the third pH and the fourth pH are set between the first pH and the second pH.
2. The method for producing the ammoxidation catalyst according to claim 1, wherein
the step of preparing the precursor slurry is a step of mixing a second solution or slurry comprising at least bismuth and iron with a first solution or slurry comprising at least molybdenum to obtain a precursor slurry,
a pH of the first solution or slurry before the second solution or slurry is mixed is within a range of 5.5-7.0, a pH of the first solution or slurry after mixing of the second solution or slurry is completed is within a range of 0.1-1.9, and a time during which a pH of a mixture passes through a range of 4.0-2.0 while the second solution or slurry is mixed is 1-70 seconds.

3. The method for producing the ammoxidation catalyst according to claim 1, wherein the step of preparing the precursor slurry is a step of mixing a second solution or slurry comprising at least molybdenum with a first solution or slurry comprising at least bismuth and iron to obtain a precursor slurry, a pH of the first solution or slurry before the second solution or slurry is mixed is within a range of 0.1-0.5, a pH of the first solution or slurry after mixing of the second solution or slurry is completed is within a range of 0.7-1.9, and a time during which a pH of a mixture passes through a range of 0.5-0.7 while the second solution or slurry is mixed is 1-70 seconds.

4. The method for producing the ammoxidation catalyst according to claim 1 or 2, wherein a volume of the precursor slurry is 10 L or more, a time during which the pH of the mixture passes through the particular range at an outermost peripheral position in a container nearest to a position where the second solution or slurry is added while the second solution or slurry is mixed is designated as a first time, a time during which the pH of the mixture passes through the particular range at an outermost peripheral position in the container farthest from the position where the second solution or slurry is added while the second solution or slurry is mixed is designated as a second time, the first time is within a range of 1-70 seconds, and a ratio of the second time to the first time is 3 or less.

5. The method for producing the ammoxidation catalyst according to claim 2 or 3, wherein in the step of preparing the precursor slurry, the solution or slurry comprising at least molybdenum comprises at least silica.

6. The method for producing the ammoxidation catalyst according to claim 1 or 2, wherein the ammoxidation catalyst comprises a metal oxide having a composition represented by the following general formula (1), and a support containing silica, $$Mo_{12}Bi_aFe_bX_cY_dZ_eO_f \qquad (1)$$

wherein X represents one or more elements selected from nickel, cobalt, magnesium, calcium, zinc, strontium, and barium, Y represents one or more elements selected from cerium, chromium, lanthanum, neodymium, yttrium, praseodymium, samarium, aluminum, gallium, and indium, Z represents one or more elements selected from potassium, rubidium, and cesium, $0.1 \leq a \leq 2.0$, $0.1 \leq b \leq 3.0$, $0.1 \leq c \leq 10.0$, $0.1 \leq d \leq 3.0$, $0.01 \leq e \leq 2.0$, and f is a number of atoms of oxygen necessary to satisfy valence requirements of other elements present.

7. A method for producing acrylonitrile, comprising reacting propylene, molecular oxygen, and ammonia, wherein the ammoxidation catalyst produced by the method according to claim 1 or 2 is used.

* * * * *